United States Patent

Gottschlich et al.

Patent Number: 5,472,961
Date of Patent: Dec. 5, 1995

[54] ACETAMIDES

[75] Inventors: Rudolf Gottschlich, Reinheim; Karl-August Ackermann, Ober-Ramstadt; Christoph Seyfried, Jugenheim; Andrew Barber, Weiterstadt; Gerd Bartoszyk; Hartmut Greiner, both of Darmstadt, all of Germany

[73] Assignee: Merck Patent Gesellschaft mit beschrankter Haftung, Darmstadt, Germany

[21] Appl. No.: 397,758

[22] Filed: Mar. 2, 1995

[30] Foreign Application Priority Data

Mar. 3, 1994 [DE] Germany .............. 44 07 047.0

[51] Int. Cl.$^6$ .................. C07D 413/14; A61K 31/42
[52] U.S. Cl. .................. 514/230.5; 544/105; 548/221; 548/306.1; 514/375; 514/387
[58] Field of Search .................. 544/105; 548/321, 548/306.1; 514/230.5, 375, 387

[56] References Cited

U.S. PATENT DOCUMENTS 4,192,883  3/1980  Cousse et al. .................. 424/274

FOREIGN PATENT DOCUMENTS 0569802  6/1995  European Pat. Off. .

Primary Examiner—C. Warren Ivy
Assistant Examiner—Zinna N. Davis
Attorney, Agent, or Firm—Millen, White, Zelano & Branigan

[57] ABSTRACT

Novel acetamides of the formula I

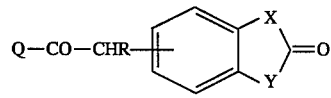

in which Q, R, X and Y have the meanings defined herein, have analgesic and neuroprotective properties and bind with high affinity to kappa receptors.

15 Claims, No Drawings

ACETAMIDES

BACKGROUND OF THE INVENTION

The invention relates to novel acetamides of the formula

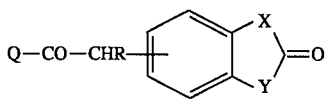

in which
Q is $R^1$—CH(CH$_2$Z)—NA—,

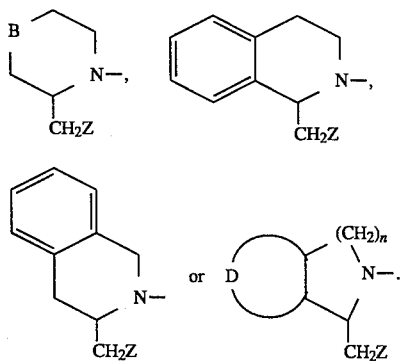

R is H, A or Ar,

X and Y are each, independent of one another, —O—, —NH—, —NA—, —CH$_2$—O—, —CH$_2$—NH— or —CH$_2$—NA—, $R^1$ is A or Ar, A is alkyl with 1 to 6 C atoms, B is —O—, —NH—, —NA—, —CH$_2$—, —N—COA—, —N—COOA— or a bond, D is a fused-on ring system with 3 to 5 C atoms, where one C atom can optionally be replaced by S, N or O, and which can optionally be substituted once or twice by F, Cl, Br, I, OH, OA, NH$_2$, NHA, NA$_2$, NH—COA, NA—COA or NH—CONH$_2$, Z is 1-pyrrolidinyl or 3-hydroxy-1-pyrrolidinyl, Ar is phenyl which is unsubstituted or substituted once or twice by A, OA or Hal, Hal is F, Cl, Br or I and n is 1 or 2 and the physiologically acceptable salts thereof.

Arylacetamides are described in DE 4215213 which corresponds to EP 569802.

SUMMARY OF THE INVENTION

It was an object of the invention to find novel compounds with valuable properties, especially those which can be used for the preparation of medicaments.

Upon further study of the specification and appended claims, further objects and advantages of this invention will become apparent to those skilled in the art.

It has been found that the compounds of the formula I and their physiologically compatible salts possess valuable pharmacological properties. They exhibit, e.g., an analgesic action and antagonise inflammation-related hyperalgesia in particular. Thus, the compounds are effective in the writhing test on mice or rats (for method see Siegmund et al., Proc. Soc. Exp. Biol. 95, (1957), 729–731). The analgesic action can also be demonstrated in the tail flick test on mice or rats (for methodology see d'Amour and Smith, J. Pharmacol. Exp. Ther. 72, (1941), 74–79) and in the hot plate test (see Schmauss and Yaksh, J. Pharmacol. Exp. Ther. 228, (1984), 1–12 and the literature cited therein). Especially potent actions are to be observed in rats in the model of carrageenin-induced hyperalgesia (see Bartoszyk and Wild, Neuroscience Letters 101 (1989) 95). In these tests, the compounds show little or no tendency to cause physical dependence. Furthermore, antiinflammatory, antiasthmatic, diuretic, anticonvulsant, neuroprotective and/or antitussive actions can also be demonstrated by methods commonly used for this purpose. The compounds show a high affinity with respect to the binding behaviour to kappa receptors and act as L-DOPA antagonists. They are, moreover, suitable for protecting against and treating cerebral oedemas and states of supply deficiency of the central nervous system, especially hypoxia, as well as for treating ischaemias.

The compounds can therefore be used as pharmacological active ingredients in human and veterinary medicine. They are also suitable as intermediates for the preparation of other compounds with valuable properties.

The invention relates to compounds of the formula I and to their salts.

The group A is alkyl with 1, 2, 3, 4, 5 or 6 C atoms, especially methyl or ethyl, but also propyl, isopropyl, butyl, isobutyl, sec-butyl or tert-butyl. Accordingly, the group OA is preferably methoxy or ethoxy, furthermore propoxy, isopropoxy, butoxy, iso-butoxy, sec-butoxy or tert-butoxy, and the group-NA- is preferably N-methyl, the group-NHA is methylamino and the group-NA$_2$ is N,N-dimethylamino.

Accordingly, the groups shown below have the preferred meanings specified as follows:

—NH—CO—A: acetamido, propionamido;

—NA—CO—A: N-methylacetamido, N-methylpropionamido.

Ar is preferably unsubstituted phenyl, also preferably o-, m- or p-methylphenyl, furthermore, preferably o-, m- or p-methoxyphenyl, o-, m- or p-fluorophenyl or o-, m- or p-chlorophenyl. Among the substituted phenyl radicals, those in the p position, but also those in the m position are preferred.

The radical R is preferably H or A, in particular methyl.

$R^1$ is particularly preferably unsubstituted phenyl, furthermore p-fluorophenyl or p-chlorophenyl, and methyl, ethyl, propyl or isopropyl.

X and Y can be identical to or different from one another. When they have the same meaning, both radicals are preferably —NH— or —NA—. If the two groups are different from one another, one of the radicals is preferably —NH— or —NA— while the other is preferably —O— or —O—CH$_2$—.

The radical Q preferably has the following meanings:

N-methyl-N-(1-phenyl-2-pyrrolidinoethyl)amino;

N-methyl-N-[1-phenyl-2-(3-hydroxypyrrolidino)-ethyl] amino;

N-methyl-N-[1-(p-chlorophenyl)-2-pyrrolidinoethyl]-amino;

N-methyl-N-[1-(p-methoxyphenyl)-2-pyrrolidinoethyl]-amino;

N-methyl-N-[1-(p-methoxyphenyl)-2-(3-hydroxypyrrolidino)ethyl]-amino;
N-methyl-N-(1-pyrrolidino-3-methyl-2-butyl)amino;
N-methyl-N-[1-(3-hydroxypyrrolidino)-3-methyl-2-butyl]amino;
2-(pyrrolidinomethyl)-1,2,3,4-tetrahydroisoquinolin-1-yl or
2-(3-hydroxypyrrolidinomethyl)-1,2,3,4-tetrahydroisoquinolin-1-yl.

Z is pyrrolidino which is preferably unsubstituted or substituted by OH in position 3.

Accordingly, the invention particularly relates to those compounds of the formula I in which at least one of the said radicals has one of the preferred meanings indicated above. Some preferred groups of compounds can be expressed by the following formulae Ia to Ie, which correspond to formula I and in which the radicals not identified precisely have the meaning indicated for formula I but in which in Ia R is H, X is —O—CH$_2$— and Y is —NH—;
in Ib R is H, X=Y and are —NH— or —NA—;
in Ic R is H, X is —O— and Y is —NH—;
in Id R is H, X is —NH— and Y is —NA—;
in Ie R is H, X is —NA— and Y is —NH—;

Further preferred compounds are those of the formulae I' and Ia' to Ie' which correspond to the formulae I and Ia to Ie, respectively, but in which Q is additionally in each case
(a) N-methyl-N-(1-phenyl-2-pyrrolidinoethyl)amino;
(b) N-methyl-N-[1-phenyl-2-(3-hydroxypyrrolidino)-ethyl]amino;
(c) N-methyl-N-(1-pyrrolidino-3-methyl-2-butyl)amino;
(d) N-methyl-N-[1-(3-hydroxypyrrolidino)-3-methyl-2-butyl]amino;
(e) N-(1-phenyl-2-pyrrolidinoethyl)amino;
(f) 2-(pyrrolidinomethyl)-1,2,3,4-tetrahydro-isoquinolin-1-yl
(g) 2-(3-hydroxypyrrolidinomethyl)-1,2,3,4-tetrahydroisoquinolin-1-yl.

The invention furthermore relates to a process for the preparation of acetamides of the formula I, and the salts thereof, characterized in that a compound of the formula II

Q—H      II in which Q has the meaning stated in formula I, is reacted with a compound of the formula III

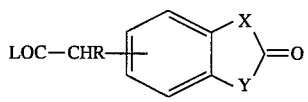

III in which

L is Cl, Br, OH, OA, NH$_2$, N$_3$, acyloxy, Ar-alkoxy with 7–11 C atoms or aroyloxy with 6–10 C atoms or another reactively esterified OH group,
and
R, X and Y have the stated meanings, or in that a radical Q, R, X and/or Y in a compound of the formula I according to formula I is converted into another radical Q, R, X and/or Y, or in that a compound which otherwise corresponds to formula I but which, in place of one or more hydrogen atoms, contains one or more solvolyzable group(s) is treated with a solvolyzing agent, and/or in that a basic compound of the formula I is converted by treatment with an acid into one of its salts.

The reaction conditions for carrying the processes described above are known per se, as described in the literature (e.g. in the standard works such as Houben-Weyl, Methoden der Organischen Chemie (Methods of Organic Chemistry), Georg-Thieme-Verlag, Stuttgart or J. March, Adv. Org. Chem. 3rd Ed., J. Wiley & Sons (1985)), i.e. under reaction conditions which are known and suitable for said reactions. It is also possible to use variants which are known per se and are not mentioned in further detail here.

The starting materials are generally known or can be prepared analogously to known substances by processes known per se. If desired, they can also be formed in situ in a manner such that they are not isolated from the reaction mixture, but immediately reacted further to give the compounds of the formula I. On the other hand, the reaction can be carried out in steps, in which case it is possible to isolate other intermediates.

The individual process variants are illustrated in further detail below.

The compounds of the formula I can preferably be prepared by reacting the compounds of the formula II with carboxylic acids of the formula III or their functional derivatives. Suitable functional derivatives of the compounds of the formula III are especially the corresponding esters, in particular the methyl or ethyl esters, and the halides, anhydrides or azides; the chlorides are preferred.

Compounds of the formula II can be obtained, for example, by reaction of 1-(chloromethyl)-1,2,3,4-tetrahydroisoquinoline with pyrrolidine or 3-hydroxypyrrolidine, of 1-amino-1-phenyl-2-pyrrolidinoethane with methyl iodide, of 1-N-methylamino-1-phenyl-2-halogenoethane (halogen is preferably Cl or Br) with pyrrolidine or 3-hydroxypyrrolidine or of 1-halogeno-2-N-methylamino-4-methylpentane with pyrrolidine or its 3-hydroxy derivative.

Compounds of the formula II can furthermore be obtained by reaction of 2-halogenomethyl derivatives of piperazine or piperidine with pyrrolidine or 3-hydroxypyrrolidine.

Examples of typical compounds of the formula III are acetic acid or phenylacetic acid derivatives such as, for example, chlorides, bromides, azides, methyl or ethyl esters or anhydrides which are additionally linked in position 2 to a radical of the formula III a

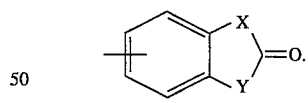

IIIa where X and Y have the stated meanings.

The compounds of the formula III can be prepared, for example, by reacting 3-, 4-, 5- or 6-halomethyl-2-aminophenols or the corresponding 3-, 4-, 5- or 6-halomethyl-o-phenylenediamine derivatives with phosgene or other reactive carbonic acid derivatives under conditions known per se, and subsequently converting the halogen radical into a carboxyl group or a derivative which can be prepared therefrom, such as, for example, an acid chloride. Compounds of the formula I are furthermore successfully prepared by, for example, reacting 3-amino-4-hydroxyphenylacetic acid or 3,4-diaminophenylacetic acid with 1,1'-carboxyl-diimidazole.

Reaction of II with III or III derivatives preferably takes place in the presence or absence of an inert organic solvent, for example of a halogenated hydrocarbon such as dichloromethane, chloroform or trichloroethene, of an alcohol such as methanol, ethanol or butanol, of an ether such as tetrahydrofuran (THF) or dioxane, of an amide such as dimethylformamide (DMF), of a sulfoxide such as dimethyl sulfoxide (DMSO) and/or in the presence or absence of a condensing agent, for example a base, at temperatures of preferably about −20°–200°, especially 0°–100°. Examples of suitable bases are alkali metal hydroxides such as NaOH or KOH, alkali metal carbonates such as $Na_2CO_3$ or $K_2CO_3$, tertiary amines such as triethylamine or pyridine. Particularly preferred as solvent is dichloromethane and as base is triethylamine.

It is furthermore possible in a compound of the formula I to convert one or more of the radicals Q, R, X and/or Y into one or more other radicals Q, R, X and/or Y.

Thus, ether groups (for example OA groups) or ester groups can be cleaved to form OH groups, for example by treatment with dimethyl sulfide/boron tribromide complex, for example in toluene, THF or DMSO, or by fusion with pyridine hydrohalides or aniline hydrohalides, preferably pyridine hydrochloride, at about 150°–250°, or by treatment with diisobutylaluminium hydride in toluene at about 0°–110°.

It is furthermore possible to etherify or esterify OH groups, for example by initially preparing the corresponding alkali metal (for example Na or K) alcoholates, phenolates or salts, and reacting the latter with appropriate halogen compounds, for example with alkyl halides such as methyl chloride, bromide or iodide, chloro- or bromoacetamide, expediently in the presence of one of the abovementioned solvents at temperatures of preferably about 0°–100°.

Nitro groups can be reduced to amino groups, preferably by catalytic hydrogenation under the above-mentioned conditions, for example with Raney Ni in methanol or ethanol at 15°–40° under atmospheric pressure.

Amino groups can be acylated, for example with acid chlorides such as acetyl or methanesulfonyl chloride, or the monoester chloride of oxalic acid or succinic acid, preferably in inert solvents such as dichloromethane at 15°–40°.

It is furthermore possible to alkylate amino groups by methods known per se.

It is additionally possible to solvolyse, in particular hydrolyse, compounds which otherwise correspond to the formula I but which contain one or more solvolysable group(s) in place of one or more H atoms to give compounds of the formula I.

Thus, in particular, 3-acylbenzoxazole derivatives (corresponding to the formula I but containing in position 3 of the benzoxazole an acyl group, preferably an alkanoyl, alkylsulphonyl or arylsulphonyl group with in each case up to 10 C atoms, such as methane-, benzene- or p-toluenesulphonyl) can be hydrolysed to the corresponding benzoxazole which is unsubstituted in position 3 of the benzoxazole ring, for example in acidic, or better in neutral or alkaline medium at temperatures of about 0°–200® C. Bases which are preferably used are sodium, potassium or calcium hydroxide, sodium or potassium carbonate or ammonia. Solvents preferably chosen are water; lower alcohols such as methanol, ethanol; ethers such as THF, dioxane; sulphones such as tetramethylene sulphone; or mixtures thereof, especially water-containing mixtures. Hydrolysis may also take place simply on treatment with water alone, especially at the boiling point.

A base of the formula I can furthermore be converted with an acid into the relevant acid addition salt. Suitable acids for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, as well as organic acids, especially aliphatic, alicyclic, araliphatic, aromatic or heterocyclic mono- or poly-basic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemonosulfonic and naphthalenedisulfonic acids and lauryl sulfuric acid. Salts with physiologically unacceptable acids, for example picrates, can be used to purify the compounds of the formula I.

If desired, the free bases of formula I can be liberated from their salts by treatment with strong bases such as sodium or potassium hydroxide or sodium or potassium carbonate.

The invention furthermore relates to the use of the compounds of the formula I and of their physiologically acceptable salts for the production of pharmaceutical preparations, in particular by non-chemical means. For this they can be converted together with at least one solid, liquid and/or semiliquid vehicle or ancillary substance and, where appropriate, in combination with one or more other active ingredients into a suitable dosage form.

The invention furthermore relates to compositions, in particular pharmaceutical preparations, which contain at least one compound of the formula I and/or one of its physiologically acceptable salts.

These preparations can be used as medicaments in human or veterinary medicine. Suitable vehicles are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc and petrolatum. Forms used for oral administration are, in particular, tablets, pills, coated tablets, capsules, powders, granules, syrups, juices or drops, forms used for rectal administration are suppositories, forms used for parenteral administration are solutions, preferably oily or aqueous solutions, as well as suspensions, emulsions or implants, and forms used for topical administration are ointments, creams or powders. The novel compounds can also be lyophilized and the resulting lyophilizates be used, for example, for preparing products for injection. The indicated preparations can be sterilized and/or contain ancillary substances such as lubricants, preservatives, stabilisers and/or wetting agents, emulsifiers, salts to influence the osmotic pressure, buffer substances, colorants, flavorings and/or aromatising substances. They can, if required, also contain one or more other active ingredients, for example one or more vitamins.

The compounds of the formula I and their physiologically acceptable salts can be used for controlling diseases, especially states of pain, but also for reducing the secondary damage after ischaemia, preferably cerebral ischaemia.

Here the substances of the invention are normally administered analogously to known analgesics, such as for example, tramadol, preferably in dosages of about 1–500 mg, especially 5–100 mg, per dosage unit. The daily dosage is preferably about 0.02–10 mg/kg of body weight. However, the particular dose for each individual patient depends on a very wide variety of factors, for example efficacy of the particular compound used, age, body weight, general state of health, sex, diet, time and route of administration, rate of excretion, drug combination and severity of the particular disease for which the therapy is intended. Oral administration is preferred.

All temperatures are given in °C. hereinbefore and hereinafter. Some compounds of the formula I tend to decompose on heating so that no clear melting points can be determined. Therefore, in these cases, as far as possible, as a substitute, the corresponding $R_f$ values (thin-layer chromatography) are given. In the following examples, "usual working up" means: water or dilute sodium hydroxide solution is added if necessary, the mixture is extracted with dichloromethane, the organic phase is separated off, dried with sodium sulfate, filtered and evaporated, and purification is by chromatography on silica gel and/or by crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 4407047.0, are hereby incorporated by reference.

EXAMPLES

EXAMPLE 1

1.6 ml of thionyl chloride are added to a suspension of 3.9 g of 2-(2,3-dihydro-2-oxobenzoxazol-5-yl)acetic acid [obtainable by reaction of methyl 3-amino-4-hydroxyphenylacetate with 1,1'-carbonyldiimidazole and subsequent hydrolysis] in 40 ml of toluene, and the mixture is boiled with stirring for 1 h. Subsequently, 1 ml of DMF is added and the mixture is heated for a further 15 min. After removal of the solvent, the residue is taken up in 25 ml of THF and added dropwise to a solution of 4 g of triethylamine and 4.4 g of (1S)-1-N-methylamino-1-phenyl-2-(3S)-3-hydroxypyrrolidino)ethane [obtainable from (1S)-1-amino-1-phenyl-2-chloroethane by reaction with (3S)-3-hydroxypyrrolidine and subsequent methylation with methyl iodide] in 40 ml of THF. After stirring for 2 hours, the solvent is removed and the usual working up is carried out. N-methyl-N-[(1S)-1-phenyl-2-((3S)-3-hydroxypyrrolidino)-ethyl]-2-(2,3-dihydro- 2-oxobenzoxazol-5-yl)-acetamide is obtained, m.p. 207°–208°.

The following are obtained analogously by reaction of 2-(2,3-dihydro-2-oxobenzoxazol-5-yl)acetic acid
with (1S)-1-N-methylamino-1-phenyl-2-pyrrolidino-ethane: N-methyl-N-[(1S)-1-phenyl-2-pyrrolidino-ethyl]-2-(2,3-dihydro-2-oxobenzoxazol-5-yl)-acetamide;
with (1S)-1-N-methylamino-1-(p-methoxyphenyl)-2-( (3S)-3-hydroxypyrrolidino)ethane: N-methyl-N-[(1S)-1-(p-methoxyphenyl )-2-( (3S)-3-hydroxypyrrolidino)ethyl]-2-( 2,3-dihydro-2-oxobenzoxazol-5-yl ) acetamide;
with 1-(pyrrolidinomethyl)-1,2,3,4-tetrahydroiso-quinoline: 1-(pyrrolidinomethyl)-2-[(2,3-dihydro-2-oxobenzoxazol-5-yl)acetyl] -1,2,3,4-tetra-hydroisoquinoline;
with 1-[(3S)-3-hydroxypyrrolidinomethyl]-1,2,3,4-tetrahydroisoquinoline: 1-[(3S)-3-hydroxypyrrolidinomethyl]-2-[(2,3-dihydro-2-oxobenzoxazol- 5-yl)acetyl]-1,2,3,4-tetrahydroisoquinoline, m.p. 130°–135° (decomposition);
with 3-[(3S)-3-hydroxypyrrolidinomethyl]-1,2,3,4-tetrahydroisoquinoline: 2-[(2,3-dihydro-2-oxobenzoxazol-5-yl)acetyl]-3-[(3S)-3-hydroxy pyrrolidinomethyl]-1,2,3,4-tetrahydroisoquinoline, m.p. 179°;
with 1-(pyrrolidinomethyl)-1,2,3,4-tetrahydroiso-quinoline: 1-(pyrrolidinomethyl)-2-[(2,3-dihydro-2-oxobenzoxazol-5-yl)acetyl] -1,2,3,4-tetra-hydroisoquinoline;
with 3-(pyrrolidinomethyl)-1,2,3,4-tetra-hydroisoquinoline: 2-[(2,3-dihydro-2-oxobenzoxazol-5-yl)acetyl]-3-(pyrrolidinomethyl)-1,2,3,4-tetrahydroiso-quinoline;
with N-methyl-N-[(2S)-1-pyrrolidino-3-methyl-2-butyl] amine: N-methyl-N-[(2S)-1-pyrrolidino-3-methyl-2-butyl]-2-(2,3-dihydro- 2-oxobenzoxazol-5-yl)acetamide;
with N-methyl-N-[2(S)-1-((3S)-3-hydroxy-pyrrolidino)-3-methyl-2-butyl]amine: N-methyl-N-[(2S)-1-((3S)-3-hydroxy-pyrrolidino)-3-methyl-2-butyl]- 2-(2,3-dihydro-2-oxobenzoxazol-5-yl)acetamide (oil), Rf: 0.45 (silica gel/ $CH_2Cl_2/CH_3OH$ 9:1; 1% $NH_3$);

EXAMPLE 2

The following are obtained in analogy to Example 1 by reaction of 2-(3-oxo-3,4-dihydro-2H-1,4-benzoxazin-6-yl)acetic acid
with (1S)-1-N-methylamino-1-phenyl-2-((3S)-3-hydroxypyrrolidino)ethane: N-methyl-N-[(1S)-1-phenyl-2-((3S)-3-hydroxypyrrolidino)ethyl]-2-(3-oxo-3,4-dihydro-2H-1,4-benzoxoxazin-6-yl)acetamide hydrochloride, m.p. 237°–239°;
with (1S)-1-N-methylamino-1-phenyl-2-pyrrolidino-ethane: N-methyl-N-[(1S)-1-phenyl-2-pyrrolidino-ethyl]-2-(3-oxo-3,4-dihydro-2H-1,4-benzoxazin- 6-yl)acetamide;
with (1S)-1-N-methylamino-1-(p-methoxyphenyl)-2-((3S)-3-hydroxypyrrolidino) ethane: N-methyl-N-[(1S)-1-(p-methoxyphenyl)-2-( (3S)-3-hydroxypyrrolidino) ethyl]-2-( 3-oxo-3,4-dihydro-2H-1,4-benzoxazin-6-yl) acetamide;
with 1-(pyrrolidinomethyl)-1,2,3,4-tetrahydroiso-quinoline: 1-(pyrrolidinomethyl)-2-[(3-oxo-3,4-dihydro-2H-1,4-benzoxazin-6-yl)acetyl]- 1,2,3,4-tetrahydroisoquinoline;
with 1-[(3S)-3-hydroxypyrrolidinomethyl]-1,2,3,4-tetrahydroisoquinoline: 1-[(3S)-3-hydroxypyrrolidinomethyl]-2-[(3-oxo-3,4-dihydro-2H-1 ,4-benzoxazin-6-yl)acetyl]-1,2,3,4-tetrahydroisoquinoline;

with 3-[(3S)-3-hydroxypyrrolidinomethyl]-1,2,3,4-tetrahydroisoquinoline: 2-[(3-oxo-3,4-dihydro-2H-1,4-benzoxazin-6-yl)acetyl]-3-[(3S)-3-hydroxypyrrolidinomethyl]-1,2,3,4-tetrahydroisoquinoline:

with 1-(pyrrolidinomethyl)-1,2,3,4-tetra-hydroisoquinoline: 1-(pyrrolidinomethyl)-2-[(3-oxo-3,4-dihydro-2H-1,4-benzoxazin-6-yl)acetyl]-1,2,3,4-tetra-hydroisoquinoline;

with 3-(pyrrolidinomethyl)-1,2,3,4-tetra-hydroisoquinoline: 2-[(3-oxo-3,4-dihydro-2H-1,4-benzoxazin-6-yl)acetyl]-3-(pyrrolidinomethyl)- 1,2,3,4-tetra-hydroisoquinoline;

with N-methyl-N-[(2S)-1-pyrrolidino-3-methyl-2-butyl]-amine: N-methyl-N-[(2S)-1-pyrrolidino-3-methyl-2-butyl]-2-(3-oxo-3,4-dihydro-2H-1,4-benzoxazin-6-yl)acetamide;

with N-methyl-N-[2(S)-1-((3S)-3-hydroxypyrrolidino)-3-methyl-2-butyl]amine: N-methyl-N-[(2S)-1-((3S)-3-hydroxypyrrolidino)-3-methyl-2-butyl] -2-(3-oxo-3,4-dihydro-2H-1,4-benzoxazin-6-yl)acetamide.

EXAMPLE 3

The following are obtained in analogy to Example 1 by reaction of 2-(2-oxo-2,3-dihydro-benzimidazol-5-yl)acetic acid with (1S)-1-N-methylamino-1-phenyl-2-((3S)-3-hydroxypyrrolidino)ethane: N-methyl-N-[(1S)-1-phenyl-2-((3S)-3-hydroxypyrrolidino)ethyl]-2-(2-oxo- 2,3-dihydro-benzimidazol-5-yl)acetamide hydrochloride, m.p. 161°;

with (1S)-1-N-methylamino-1-phenyl-2-pyrrolidino-ethane: N-methyl-N-[(1S)-1-phenyl-2-pyrrolidino-ethyl]-2-(2-oxo-2,3-dihydrobenzimidazol-5-yl)-acetamide, m.p. 190°;

with (1S)-1-N-methylamino-1-(p-methoxyphenyl)-2-((3S)-3-hydroxypyrrolidino)ethane: N-methyl-N-[(1S)-1-(p-methoxyphenyl)-2-((3S)-3-hydroxypyrrolidino)ethyl]-2-(2-oxo-2,3-dihy with 1-(pyrrolidinomethyl)-1,2,3,4-tetra-hydroisoquinoline: 1-(pyrrolidinomethyl)-2-[(2-oxo-2,3-dihydro-benzimidazol-5-yl)acetyl]-1,2,3,4-tetrahydroiso-quinoline;

with 1-[(3S)-3-hydroxypyrrolidinomethyl]-1,2,3,4-tetrahydroisoquinoline: 1-[(3S)-3-hydroxypyrrolidinomethyl]-2-[(2-oxo-2,3-dihydrobenzimidazol-5-yl)acetyl]-1,2,3,4-tetrahydroisoquinoline;

with 3-[(3S)-3-hydroxypyrrolidinomethyl]-1,2,3,4-tetrahydroisoquinoline: 2-[(2-oxo-2,3-dihydrobenzimidazol-5-yl)-acetyl]-3-[(3S)-3-hydroxypyrrolidinomethyl]-1,2,3,4-tetrahydroisoquinoline;

with 1-(pyrrolidinomethyl)-1,2,3,4-tetrahydroiso-quinoline: 1-(pyrrolidinomethyl)-2-[(2-oxo-2,3-dihydro-benzimidazol-5-yl)acetyl]-1,2,3,4-tetrahydroiso-quinoline;

with 3-(pyrrolidinomethyl)-1,2,3,4-tetrahydroiso-quinoline: 2-[(2-oxo-2,3-dihydrobenzimidazol-5-yl)-acetyl]-3-(pyrrolidinomethyl)-1,2,3,4-tetra-hydroisoquinoline;

with N-methyl-N-[(2S)-1-pyrrolidino-3-methyl-2-butyl]-amine: N-methyl-N-[(2S)-1-pyrrolidino-3-methyl-2-butyl]-2-(2-oxo-2,3-dihydrobenzimidazol-5-yl)acetamide;

with N-methyl-N-[2(S)-1-((3S)-3-hydroxypyrrolidino)-3-methyl-2-butyl]amine: N-methyl-N-[(2S)-1-((3S)-3-hydroxypyrrolidino)-3-methyl-2-butyl]-2-(2-oxo- 2,3-dihydrobenzimidazol-5-yl)acetamide.

EXAMPLE 4

The following are obtained in analogy to Example 1 by reaction of 2-(1-methyl-2-oxo-2,3-dihydrobenzimidazol-5-yl)acetic acid with (1S)-1-N-methylamino-1-phenyl-2-((3S)-3-hydroxypyrrolidino)ethane: N-methyl-N-[(1S)-1-phenyl-2-((3S)-3-hydroxypyrrolidino)ethyl]-2-(1-methyl-2-oxo- 2,3-dihydro-benzimidazol-5-yl)acetamide, m.p. 220°;

with (1S)-1-N-methylamino-1-phenyl-2-pyrrolidino-ethane: N-methyl-N-[(1S)-1-phenyl-2-pyrrolidino-ethyl]-2-(1-methyl-2-oxo-2,3-dihydrobenzimidazol-5-yl)acetamide, m.p. 278°;

with (1S)-1-N-methylamino-1-(p-methoxyphenyl)-2-((3S)-3-hydroxypyrrolidino)ethane: N-methyl-N-[(1S)-1-(p-methoxyphenyl)-2-((3S)-3-hydroxypyrrolidino)ethyl]-2-(1-methyl- 2-oxo-2,3-dihydrobenzimidazol-5-yl)acetamide;

with 1-(pyrrolidinomethyl)-1,2,3,4-tetrahydroiso-quinoline: 1-(pyrrolidinomethyl)-2-[(1-methyl-2-oxo-2,3-dihydrobenzimidazol- 5-yl)acetyl]-1,2,3,4-tetrahydroiso-quinoline;

with 1-[(3S)-3-hydroxypyrrolidinomethyl]-1,2,3,4-tetrahydroisoquinoline: 1-[(3S)-3-hydroxypyrrolidinomethyl]-2-[(1-methyl-2-oxo-2,3-dihydrobenzimidazol-5-yl)acetyl]-1,2,3,4-tetrahydroisoquinoline;

with 3-[(3S)-3-hydroxypyrrolidinomethyl]-1,2,3,4-tetrahydroisoquinoline: 2-[(1-methyl-2-oxo-2,3-dihydrobenzimidazol-5-yl)acetyl]-3-[(3S )-3-hydroxypyrrolidinomethyl]-1,2,3,4-tetrahydroisoquinoline;

with 1-(pyrrolidinomethyl)-1,2,3,4-tetrahydroiso-quinoline: 1-(pyrrolidinomethyl)-2-[(1-methyl-2-oxo-2,3-dihydrobenzimidazol- 5-yl)acetyl]-1,2,3,4-tetrahydroiso-quinoline;

with 3-(pyrrolidinomethyl)-1,2,3,4-tetrahydroiso-quinoline: 2-[(1-methyl-2-oxo-2,3-dihydrobenzimidazol-5-yl)acetyl]-3-(pyrrolidinomethyl)- 1,2,3,4-tetra-hydroisoquinoline;

with N-methyl-N-[(2S)-1-pyrrolidino-3-methyl-2-butyl]-amine: N-methyl-N-[(2S)-1-pyrrolidino-3-methyl-2-butyl]-2-(1-methyl-2-oxo-2,3-dihydrobenzimidazol-5-yl)acetamide;

with N-methyl-N-[2(S)-1-((3S)-3-hydroxypyrrolidino)-3-methyl-2-butyl]amine: N-methyl-N-[(2S)-1-((3S)-3-hydroxypyrrolidino)-3-methyl-2-butyl] -2-(1-methyl-2-oxo-2,3-dihydrobenzimidazol-5-yl)acetamide.

EXAMPLE 5

3.1 g of 2-(3-oxo-3,4-dihydro-2H-1,4-benzoxazin-6-yl)acetohydrazide [for example obtainable from the corresponding ethyl ester by reaction with hydrazine] are dissolved in 200 ml of very dilute hydrochloric acid and, while stirring at 0°, a solution of 2.0 g of NaNO₂ in 40 ml of water is added dropwise, the mixture is stirred for 30 min., and the azide which has formed is extracted with dichloromethane. After drying over MgSO₄ and concentrating to 50 ml, the reagent obtained in this way is added dropwise to a solution of (1S)-1-N-methylamino-1-(2,4-dichlorophenyl)-2-((3S)-3-hydroxypyrrolidino)ethane and 4 ml of tri-ethylamine in 100 ml of dichloromethane. The mixture is then stirred at room temperature for 2 h, and the usual working up results in N-methyl-N-[(1S)-1-(2,4-dichlorophenyl)-2-((3S)-3-hydroxypyrrolidino)ethyl]-2-(3-oxo- 3,4-dihydro-2H-1,4-benzoxazin- 6-yl)acetamide.

EXAMPLE 6

A solution of 1 g of N-methyl-N-[(1S)-1-(p-benzyloxyphenyl)-2-((3S)-3-benzyloxypyrrolidino)ethyl]-2-(2-oxo-2,3-dihydrobenzimidazol- 5-yl)acetamide in 25 ml of ethyl acetate is hydrogenated on 0.5 g of 5% Pd—C at 20° and under 1 bar until hydrogen uptake ceases, the mixture is filtered, the filtrate is evaporated, and N-methyl-N-[(1S)-1-(p-hydroxyphenyl)-2-((3S)-3-hydroxypyrrolidino)ethyl]-2-(2-oxo-2,3-dihydrobenzimidazol-5-yl)acetamide is obtained.

EXAMPLE 7

3.2g of N-[(1S)-1-phenyl-2-((3S)-3-hydroxypyrrolidino-)ethyl]-2-(2-oxo- 2,3-dihydrobenzimidazol-5-yl)acetamide are dissolved in 150 ml of dichloromethane and, while stirring, 3 equivalents of methyl iodide dissolved in 20 ml of dichloromethane is added dropwise, the solution is concentrated, and the usual working up results in N-methyl-N-[(1S)-1-phenyl-2-((3S)-3-hydroxypyrro-lidino)ethyl]-2-(1,3-dimethyl-2-oxo- 2,3-dihydrobenzimidazol-5-yl)acetamide.

EXAMPLE 8

0.9 g of N-methyl-N-[(1S)-1-phenyl-2-((3S)-3-hydroxypyrrolidino)ethyl]-2-(2,3-dihydro-2-oxobenzoxazol-5yl)acetamide is dissolved in 50 ml of ethanolic HCl solution and stirred at room temperature for 6 h. After removal of the solvent and washing with a little ethanol, drying results in N-methyl-N-[(1S)-1-phenyl-2-((3S)-3-hydroxypyrrolidino-)ethyl]-2-(2,3-dihydro-2-oxobenzoxazol-5-yl)acetamide hydrochloride, m.p. 263°.

The following examples relate to pharmaceutical preparations:

Example A: Vials

A solution of 100 g of an active substance of the formula I and 5 g of disodium hydrogen phosphate in 3 l of double distilled water is adjusted to pH 6.5 with 2N hydrochloric acid, filtered sterile, dispensed into vials, lyophilized under sterile conditions and sealed sterile. Each vial contains 5 mg of active substance.

Example B: Suppositories

A mixture of 20 g of an active substance of the formula I with 100 g of soya lecithin and 1400 g of cocoa butter is melted, poured into moulds and left to cool. Each suppository contains 20 mg of active substance.

Example C: Solution

A solution of 1 g of an active substance of the formula I, 9.38 g of $NaH_2PO_4 \cdot 2H_2O$, 28.48 g of $Na_2HPO_4 \cdot 12H_2O$ and 0.1 g of benzalconium chloride in 940 ml of double distilled water is prepared. The pH is adjusted to 6.8, the volume is made up to 1, l and the solution is sterilized by irradiation. This solution can be used in the form of eye drops.

Example D: Ointment 500 mg of an active substance of the formula I are mixed with 99.5 g of petrolatum under aseptic conditions.

Example E: Tablets

A mixture of 1 kg of active substance of the formula I, 4 kg of lactose, 1.2 kg of potato starch, 0.2 kg of talc and 0.1 kg of magnesium stearate is compressed to tablets in a conventional way such that each tablet contains 10 mg of active substance.

Example F: Coated tablets

Tablets are produced by compression in analogy to Example E and are then covered in a conventional way with a coating of sucrose, potato starch, talc, tragacanth and colorant.

Example G: Capsules 2 kg of active substance of the formula I are packed into hard gelatin capsules in a conventional way so that each capsule contains 20 mg of the active substance.

Example H: Ampoules

A solution of 1 kg of active substance of the formula I in 60 l of double-distilled water is filtered sterile, dispensed into ampoules, lyophilized under sterile conditions and sealed sterile. Each ampoule contains 10 mg of active substance.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An acetamide compound according to formula I

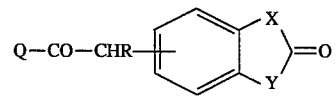

wherein

Q is $R_1$—CH($CH_2$Z)—NA—,

R is H, A or Ar

X and Y are each, independently of one another, —O—, —NH—, —NA—, —$CH_2$—O—, —$CH_2$—NH— or —$CH_2$—NA—, $R^1$ is A or Ar, A is alkyl having 1 to 6 C atoms, Z is 1-pyrrolidinyl or 3-hydroxy-1-pyrrolidinyl, Ar is phenyl, unsubstituted or substituted once or twice by A, OA or Hal, Hal is F, Cl, Br or I and n is 1 or 2, or a physiologically acceptable salt thereof.

2. A compound according to claim 1, wherein said compound is:

(a) N-methyl-N-[(1S)-1phenyl-2-((3S)-3-hydroxypyrrolidino)ethyl]-2-(2,3-dihydro-2-oxobenzoxazol- 5-yl)acetamide or a physiologically acceptable salt thereof;

(b) N-methyl-N-(2S)-[1-((3S)-3-hydroxypyrrolidino-3-methyl-2-butyl]-2-(2,3-dihydro-2-oxobenzoxazol-5-yl)acetamide or a physiologically acceptable salt thereof;

(c) N-methyl-N-[(1S)-1-phenyl-2-((3S)-3-hydroxypyrrolidino)ethyl]-2-(2,3-dihydro-2-oxobenzimidazol-5-yl)acetamide or a physiologically acceptable salt thereof;

(d) N-methyl-N-[(1S)-1-phenyl-2-((3S)-3-hydroxypyrrolidino)ethyl]-2-(2,3-dihydro-1-methyl-2-oxobenzimidazol-5-yl)acetamide or a physiologically acceptable salt thereof; or (e) N-methyl-N-[(1S)-1-phenyl-2-pyrrolidinoethyl ]-2

(2,3-dihydro-1-methyl-2-oxobenzimidazol-5-yl) acetamide or a physiologically acceptable salt thereof.

3. A compound according to claim 1, wherein

R is H, X is —O—$CH_2$— and Y is —NH—;
R is H, X=Y and are —NH— or —NA—;
R is H, X is —O— and Y is —NH—;
R is H, X is —NH— and Y is —NA—; or
R is H, X is —NA— and Y is —NH—.

4. A compound according to claim 3, where Q is (a) N-methyl-N-(1-phenyl-2-pyrrolidinoethyl)amino;
(b) N-methyl-N-[1-phenyl-2-(3-hydroxypyrrolidino)ethyl]amino;
(c) N-methyl-N-(1-pyrrolidino-3-methyl-2-butyl)amino;
(d) N-methyl-N-[1-(3-hydroxypyrrolidino)-3-methyl-2-butyl]amino; and
(e) N-(1-phenyl-2-pyrrolidinoethyl)amino.

5. A pharmaceutical composition, comprising a compound of claim 1 and a pharmaceutically acceptable vehicle.

6. A pharmaceutical composition, comprising a compound of claim 2 and a pharmaceutically acceptable vehicle.

7. A pharmaceutical composition, comprising a compound of claim 3 and a pharmaceutically acceptable vehicle.

8. A pharmaceutical composition, comprising a compound of claim 4 and a pharmaceutically acceptable vehicle.

9. A pharmaceutical composition according to claim 5, wherein the composition is a solid, liquid, or semi-liquid.

10. A pharmaceutical composition according to claim 5, further comprising an additional active ingredient.

11. A method of relieving pain or producing analgesia, comprising administering an effective amount of a compound according to claim 1.

12. A method of relieving pain or producing analgesia, comprising administering an effective amount of a compound according to claim 2.

13. A method of reducing secondary damage after ischaemia, comprising administering an effective amount of a compound according to claim 1.

14. A method for reducing secondary damage after ischaemia, comprising administering an effective amount of a compound according to claim 2.

15. A method of binding a compound according to formula I of claim 1 to a kappa receptor, comprising administering an effective amount of said compound, wherein said amount is effective in producing analgesia or reducing secondary damage after ischaemia.

* * * * *